United States Patent [19]

Morman

[11] Patent Number: 4,652,487
[45] Date of Patent: Mar. 24, 1987

[54] GATHERED FIBROUS NONWOVEN ELASTIC WEB

[75] Inventor: Michael T. Morman, Alpharetta, Ga.

[73] Assignee: Kimberly-Clark Corporation, Neenah, Wis.

[21] Appl. No.: 760,445

[22] Filed: Jul. 30, 1985

[51] Int. Cl.$^4$ ............................................. B32B 3/10
[52] U.S. Cl. .................................... 428/138; 156/161;
156/163; 156/164; 156/168; 156/183; 156/344;
428/137; 428/284; 428/285; 428/286; 428/287;
428/296; 428/297; 428/298; 428/299; 428/903;
428/913; 604/358; 604/365
[58] Field of Search ............... 428/137, 138, 256, 284,
428/285, 286, 287, 296, 297, 299, 903, 913;
604/358, 365; 156/161, 163, 164, 183, 168, 344

[56] References Cited

U.S. PATENT DOCUMENTS

| | | |
|---|---|---|
| 1,544,312 | 12/1925 | Gray. |
| 1,911,227 | 9/1933 | Galligan. |
| 2,022,852 | 12/1935 | Galligan. |
| 2,030,746 | 2/1936 | Galligan. |
| 2,957,512 | 10/1960 | Wade. |
| 3,316,136 | 4/1967 | Pufahl. |
| 3,468,748 | 9/1969 | Bassett. |
| 3,485,706 | 12/1969 | Evans. |
| 3,673,026 | 6/1972 | Brown. |
| 3,676,242 | 7/1972 | Prentice. |
| 3,687,797 | 8/1972 | Wideman. |
| 3,842,832 | 10/1974 | Wideman. |
| 3,849,241 | 11/1974 | Butin. |
| 4,104,170 | 8/1978 | Nedza. |
| 4,209,563 | 6/1980 | Sisson. |
| 4,296,163 | 10/1981 | Emi. |
| 4,305,990 | 12/1981 | Kelly. |
| 4,323,534 | 4/1982 | Des Marais ..................... 264/176 R |
| 4,340,563 | 1/1982 | Appel et al. .......................... 264/518 |
| 4,355,425 | 10/1982 | Jones ........................................ 2/402 |
| 4,379,192 | 4/1983 | Wahlquist .......................... 418/156 |
| 4,413,623 | 11/1983 | Pieniak ................................. 604/365 |
| 4,418,123 | 11/1983 | Bunnelle ............................. 418/517 |
| 4,426,420 | 1/1984 | Likhyani ............................ 428/224 |
| 4,446,189 | 5/1984 | Romanek ............................ 428/152 |
| 4,450,026 | 5/1984 | Pieniak .............................. 156/164 |

FOREIGN PATENT DOCUMENTS 2260716 2/1981 Fed. Rep. of Germany.
47-43150 1/1983 Japan.

OTHER PUBLICATIONS

Shell Technical Bulletin, SC:763-83, Kraton DX 1117.
Shell Technical Bulletin, SC:607-84, Kraton GX 1657.
Shell Technical Bulletin, SC:606-84, Kraton D 1116.
Shell Technical Bulletin, SC:605-82, Kraton DX 1112.
Shell Technical Bulletin, SC:604-82, Kraton D 1111.
Shell Technical Bulletin, SC:455-81, Kraton, Processing & Fabricating Kraton Thermoplastic Rubber Compounds.
Shell Technical Bulletin, SC:198-83, Kraton, An Extremely Versatile Polymen . . . Etc.
Shell Technical Bulletin, SC:165-77, Kraton, Rubber for Modification of Thermoplastics.
Shell Technical Bulletin, SC:72-85, Solution Behavior of Kraton Thermoplastic Rubbers.
Shell Technical Bulletin, SC:70-83, Kraton D 1101.
Shell Technical Bulletin, SC:68-85, Typical Properties of Kraton Materials, 1985.
Shell Technical Bulletin, SC:39-85, Kraton G 1652.
Shell Technical Bulletin, SC:38-82, Kraton G 1650.

*Primary Examiner*—James J. Bell
*Attorney, Agent, or Firm*—Joseph P. Harps

[57] ABSTRACT

A process for producing a gathered nonwoven web having elastic characteristics is disclosed. The process includes the steps of (a) providing an extendable and retractable or contractable forming surface; (b) extending the forming surface to its extended length; (c) forming a fibrous nonwoven gatherable web directly upon a surface of the forming surface while maintaining the forming surface at its extended length to separably join the fibrous nonwoven gatherable web to the forming surface while continuing to maintain the forming surface at its extended length; (d) contracting the forming surface to its contracted length to gather the fibrous nonwoven gatherable web and (e) separating the gathered fibrous nonwoven web from the forming surface. The gathered fibrous nonwoven web formed by the disclosed process is also disclosed and described.

23 Claims, 5 Drawing Figures

GATHERED FIBROUS NONWOVEN ELASTIC WEB

FIELD OF THE INVENTION

The field of the present invention encompasses processes for forming gathered nonwoven elastic webs and the gathered nonwoven elastic webs formed by such processes.

BACKGROUND OF THE INVENTION

There has been a desire in the area of diaper fabrication to provide a web for use in diaper fabrication which is (1) elastic over its entire surface—to provide a tight yet comfortable fit; (2) water repellent—to retain fluid materials within the confines of the diaper; (3) breathable—to allow an exchange of vapors through the diaper material; (4) soft—for improved comfort and (5) inexpensive to manufacture—so that that diaper may be economically marketed to the consumer.

Unfortunately, the known nonwoven materials which have, to date, been marketed have been lacking in one or more of these characteristics. Furthermore, these nonwoven materials have generally been formed from elastomeric materials and have not been formed by utilization of the novel and economical processes of the present invention.

For example, U.S. Pat. No. 2,957,512 to Wade discloses a method for producing an elastic composite sheet material in which a creped or corrugated flexible sheet material is bonded to, for example, an elastic meltblown material. It is stated at column 4, lines 60-65 of the patent that in formation of the structures illustrated in FIGS. 2-6 the elastomeric material is maintained in a relaxed condition during the bonding. At column 5, lines 39-48, it is stated that the fibrous web of elastomeric material may be stretched and bonded to the corrugated web at spaced points or areas and, upon allowing the fibrous elastomeric web to relax, the composite web will assume the structure illustrated in FIG. 7.

Yet another method for forming a composite elastic fabric is disclosed in U.S. Pat. No. 3,316,136 to Pufahl. The preferred method of fabrication of this fabric involves the utilization of an adhesive which is first applied in a predetermined pattern to an elastic backing material and the elastic backing material is then stretched to an elongated state. While the elastic material is in the stretched, elongated state an overlying fabric is placed in contact therewith and held in pressurized engagement with the elastic material for a time period sufficient to insure adhesion of the two layers. Thereafter, upon drying of the applied adhesive, the tension on the elastic backing material is released causing the overlying fabric to gather in the areas outlined by the adhesive.

U.S. Pat. No. 3,485,706 to Evans at example 56 discloses the fabrication of an elongatable nonwoven, multilevel patterned structure having elasticity in one direction from an initially layered material. The structure is composed of two webs of polyester staple fibers which have a web of spandex yarn located therebetween. The webs are joined to each other by application of hydraulic jets of water which entangle the fibers of one web with the fibers of an adjacent web. During the entanglement step of fabrication the spandex yarn is prestretched 200 percent.

U.S. Pat. No. 3,673,026 to Brown discloses a method for manufacturing a laminated fabric and specifically discloses a method for manufacturing a nonwoven laminated fabric of controlled bulk. In this method separate webs of nonwoven material, e.g. creped tissue or bonded synthetic fiber, are elastically stretched to different degrees of elongation and laminated by bonding to one another while in their differentially stretched states. The bonded webs are thereafter relaxed so as to produce different degrees of contraction in each web with resultant separation of the webs in the unbonded regions and controlled bulk in the laminate. It is stated that the differential stretching includes the situation where only one web is actually stretched and the other web is maintained slack or nearly so.

U.S. Pat. No. 3,687,797 to Wideman discloses a method for producing a resilient cellulosic wadding product obtained by laminating a lower cellulosic wadding web to a prestretched polyurethane foam web. The process involves applying adhesive in a desired pattern to either of the webs with the wadding web then being laminated to the prestretched polyurethane foam web. During lamination of the wadding web to the polyurethane foam web the foam web is maintained in a stretched condition. After lamination of the two webs, the tension on the prestretched polyurethane foam web is released to cause a contraction of the foam web. The adhesive retains the wadding product and foam together while permitting bulking in areas between the adhesive zones. The stresses still remaining in the product after contraction may be further relieved by wetting.

U.S. Pat. No. 3,842,832 to Wideman is directed to a disposable stretch product such as a bandage and a method for production of the product. The product is manufactured by passing a longitudinally oriented nonwoven material over a roller so as to apply an adhesive to one surface of the nonwoven material. At the same time a polyurethane web is heated and longitudinally stretched and adhered to the nonwoven material. Thereafter, a second nonwoven material is adhered to the other surface of the polyurethane web to form a laminate consisting of a stretched inner polyurethane core and outer unstretched nonwoven fabric layers adhered to the core by the adhesive. Next, the laminate is passed through a moistening device which results in a relaxing of the engagement between the nonwoven fabric outer layers and the adhesive connecting the outer layers to the stretched polyurethane core layer. This allows the stretched polyurethane layer to return to substantially its original length which results in the outer nonwoven layers being buckled or undulated to form wrinkles.

U.S. Pat. No. 4,104,170 to Nedza discloses a liquid filter having an improved extended polypropylene element. Fabrication of the polypropylene element is accomplished by forming a spunbonded underlayer of a continuous polypropylene fiber which adheres to itself as it is laid down in a random pattern. Thereafter, an overlayer of short polypropylene fibers is deposited onto the underlayer by, for example, meltblowing the overlayer onto an extended sheet of the underlayer.

A method for producing an elastic cloth structure which includes fibers of a synthetic, organic, relatively elastomeric polymer and fibers of a synthetic, organic, elongatable, but relatively nonelastic polymer is disclosed in U.S. Pat. No. 4,209,563 to Sisson. The method includes the steps of forwarding the relatively elastic fibers and elongatable but relatively non-elastic fibers for a well dispersed random lay-down on a porous forming surface of an unbonded web having random fiber crossings. Thereafter, at least some of the fiber crossings are bonded to form a coherent bonded cloth web which is stretched to elongate some of the fibers in at least one direction and then released so that retraction of the web by the relatively elastomeric fibers provides for looping and bunching of the elongatable relatively nonelastic fibers. Forwarding of the fibers to the porous forming surface is positively controlled, and this positive control is contrasted at column 7, lines 19–33 of the patent to the use of air streams to convey the fibers. It is also stated at column 9, line 44 et. seq. of the patent that bonding of the filaments to form the coherent cloth may utilize embossing patterns or smooth heated roll nips.

U.S. Pat. No. 4,296,163 to Emi et al. discloses a fibrous composite having a coalesced assembly of (A) a sheet-like mesh structure composed of fibers of a synthetic elastomeric polymer, the individual fibers of which are interconnected at random in irregular relationship to form a number of meshes of different sizes and shape with the mesh structure having a recovery ratio after 10% stretch of at least 70% in two arbitrarily selected, mutually perpendicular directions on the plane of the mesh structure, and (B) a mat-, web- or sheet-like fiber structure composed of short or long fibers, with the fiber structure having a recovery ratio after 10% stretch of less than 50% in at least one arbitrarily selected direction. It is stated that the elastic composite is suitable as various aparrel base materials and industrial materials such as filter cloths, adsorbents and heat insulating materials. Methods for forming the composite are described at column 6, line 64 et seq. and these methods include spun bonding, see column 9, lines 15–41.

U.S. Pat. No. 4,323,534 to DesMarais discloses an extrusion process for a thermoplastic resin composition for fabric fibers with exceptional strength and good elasticity. At column 8 under the subtitle "Fiber-Forming" meltblowing of a compounded resin comprising 79.13% KRATON G-1652, 19.78% stearic acid, 0.98% titanium dioxide and 0.1% Irganox 1010 antioxidant is disclosed. It is stated that individual fibers were extruded from the meltblowing die.

U.S. Pat. No. 4,355,425 to Jones discloses a panty with a built-in elastic system to minimize gathering and to provide a comfortable, conforming fit and a method for assembling the panty. It is stated that a material made of meltblown KRATON rubber is well suited for the panty fabric material. It is also stated that a process for making meltblown KRATON fabrics is disclosed and shown schematically in FIG. 8 of the patent. The process which appears to utilize KRATON G-1652 is discussed starting at column 4, line 67 of the patent.

U.S. Pat. No. 4,379,192 to Wahlquist discloses a method for forming an impervious absorbent barrier fabric embodying film and fibrous webs where one or more meltblowing dies meltblow discontinuous fibers of small diameter as a mat directly on a prebonded web of continuous filaments. At column 3, lines 35–40 of the patent it is stated that by forming the microfiber mat directly onto the prebonded continuous filament web, primary bonds are created between the microfibers and the continuous filaments which attach the microfiber mat to the continuous filament web.

U.S. Pat. No. 4,426,420 to Likhyani discloses hydraulically entangled spunlaced fabrics composed of at least two types of staple fibers and processes for their formation which include heat treating elastomeric fibers, which behave as ordinary staple fibers until they are heat treated, to impart improved stretch and resilience properties to the fabric. The method includes the steps of drawing a potentially elastomeric fiber and allowing it to relax between the drawing and wind-up steps.

U.S. Pat. No. 4,446,189 to Romanek discloses a nonwoven textile fabric laminate which includes at least one layer of nonwoven textile fabric which is secured by needle punching to an elastic layer so that the nonwoven layer of textile fabric will be permanently stretched when the elastic layer is drafted within its elastic limits. When the elastic layer is allowed to relax and return to substantially its condition prior to being drafted the nonwoven fabric layer is stated to exhibit increased bulk as a result of its concurrent relaxation. It is also stated that the nonwoven textile fabric laminate may be utilized to form wearing apparel which has enhanced freedom of movement.

The abstract of Japanese document No. 47-43150 discloses a method for producing a nonwoven fabric having high tenacity with the method being carried out by (a) monaxially stretching a sheet or film made of a mixture of incompatible polymers, (b) laminating this sheet or material with a layer of foamed polymer, (c) stretching the laminate at right angles to the direction of orientation of the substrate and then (d) stretching in the direction orientation of the substrate. Preferred polymers are stated to include polyamides, linear polyesters, and polyolefins. Preferably, the upper layer is a polypropylene foam.

A Shell Chemical Company brochure entitled "KRATON Thermoplastic Rubber" generally discusses thermoplastic KRATON materials. This brochure is code designated by "SC: 198-83 printed in U.S.A. 7/83 SM".

While the above-discussed documents may disclose products and processes which exhibit some of the characteristics or method steps of the present invention none of them discloses or implies (a) the presently claimed processes for forming a gathered nonwoven web from nonelastic materials where the thus-formed gathered web possesses elastic characteristics or (b) the gathered nonwoven elastic webs resulting from these processes.

DEFINITIONS

The terms "elastic" and "elastomeric" and "elastic characteristics" are used interchangeably herein to mean any material which, upon application of a biasing force, is stretchable to a stretched, biased length which is at least about 125 percent, that is about one and one quarter, of its relaxed, unbiased length, and which will recover at least 40 percent of its elongation upon release of the stretching, elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length and many of these will recover to substantially their original relaxed length upon release of the stretching, elongating force and this latter class of materials is generally preferred for purposes of the present invention.

As used herein the terms "nonelastic" and "nonelastomeric" mean any material which is not encompassed by the terms "elastic" and "elastomeric" as defined herein.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have a stretched length that is 150 percent of its relaxed length. If this exemplary stretched material contracted, that is recovered, to a length of one and one tenth (1.1) inches after release of the biasing and stretching force, the material would have recovered 80 percent (0.4 inch) of its elongation.

As used herein the term "meltblown microfibers" refers to small diameter fibers having an average diameter not greater than about 100 microns, preferably having a diameter of from about 0.5 microns to about 50 microns, more preferably having an average diameter of from about 4 microns to about 40 microns and which are made by extruding a molten thermoplastic material through a plurality of fine, usually circular, capillaries as filaments into a high velocity gas (e.g. air) stream which attenuates the filaments of molten thermoplastic material to reduce their diameter to the range stated above. Thereafter, the microfibers are carried by the high velocity gas stream and are deposited on a collecting surface to form a web of randomly disbursed meltblown microfibers. Such a process is disclosed, for example, in U.S. Pat. No. 3,849,241 to Butin and the disclosure of this patent is hereby incorporated by reference.

As used herein the term "styrenic moiety" means a monomeric unit represented by the formula:

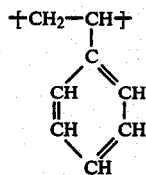

As used herein the term "spunbonded microfibers" refers to small diameter fibers having a diameter not greater than about 100 microns, preferably having a diameter of from about 10 microns to about 50 microns, more preferably having a diameter of from about 12 microns to about 30 microns and which are made by extruding a molten thermoplastic material as filaments through a plurality of fine, usually circular, capillaries of a spinnerette with the diameter of the extruded filaments then being rapidly reduced as by, for example, eductive drawing or other well known spunbonding mechanisms. The production of spunbonded nonwoven webs is illustrated in U.S. Pat. No. 4,340,563 and the disclosure of this patent is hereby incorporated by reference.

As used herein the term "nonwoven web" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web or a carded web of staple fibers. These nonwoven webs have an average basis weight of not more than 300 grams per square meter. Preferably, the nonwoven webs have an average basis weight of from about 5 grams per square meter to about 100 grams per square meter. More preferably, the nonwoven webs have an average basis weight of from about 10 grams per square meter to about 75 grams per square meter.

Unless specifically set forth and defined or otherwise limited, the terms "polymer" or "polymer resin" as used herein generally include, but are not limited to, homopolymers, copolymers, such as, for example, block, graft, random and alternating copolymers, terpolymers, etc. and blends and modifications thereof. Furthermore, unless otherwise specifically limited, the terms "polymer" or "polymer resin" shall include all possible geometrical configurations of the material. These configurations include, but are not limited to, isotactic, syndiotactic and random symmetries.

As used herein the term "consisting essentially of" does not exclude the presence of additional materials which do not significantly affect the elastic properties and characteristics of a given composition. Exemplary materials of this sort would include, without limitation, pigments, antioxidants, stabilizers, surfactants, waxes, flow promoters, solid solvents, particulates and materials added to enhance processability of the composition.

OBJECTS OF THE INVENTION

Accordingly, it is a general object of the present invention to provide a new process for forming a gathered nonwoven web possessing elastic properties.

One other general object of the present invention is to provide a new process for forming a gathered nonwoven web possessing elastic characteristics solely from nonelastic materials.

Another general object of the present invention is to provide a new process for forming a gathered nonwoven elastic web which process includes forming a nonwoven gatherable web directly on a surface of a nonwoven elastic web while the nonwoven elastic web is being maintained in a stretched, biased condition so as to separably join the gatherable web to the nonwoven elastic web and thereafter relaxing the nonwoven elastic web from its stretched, biased condition or length to a relaxed, unbiased condition or length so that the gatherable web is gathered and separating the gathered web from the elastic web to form a gathered web having elastic properties.

Yet another general object of the present invention is to provide a new process for forming a gathered nonwoven elastic web which process includes forming a gatherable web directly on the surface of an extendable and retractable porous forming surface while the forming surface is being maintained in the extended condition so as to separably join the gatherable web to the extendable and retractable forming surface, retracting the forming surface to gather the gatherable web and thereafter separating the gathered web from the forming surface to form a gathered web having elastic properties.

A further general object of the present invention is to provide the gathered nonwoven webs possessing elastic characteristics formed by the processes of the present invention.

Still further general objects and the broad scope of applicability of the present invention will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

The present invention is directed to a process for producing a gathered fibrous nonwoven web possessing elastic characteristics. An important feature of the process of the present invention is that the fibrous nonwoven gathered web is formed, in a gatherable condition, directly onto an extendable and contractable forming surface while the forming surface is maintained in the extended condition. In one embodiment the extendable and contractable forming surface is a nonwoven elastic web such as, for example, a fibrous nonwoven elastic web. In another embodiment the extendable and contractable forming surface is a extendable and contractable mesh screen forming surface.

When the gathered fibrous nonwoven web is to be formed directly on a surface of a nonwoven elastic web the nonwoven elastic web may first be formed by, for example, a meltblowing process or any other process for forming a nonwoven elastic web. For example, the nonwoven elastic web could be an apertured web of an elastic film as opposed to a meltblown fibrous nonwoven elastic web. The nonwoven elastic web, as formed, has a normal contracted, nonbiased length. Thereafter, the nonwoven elastic web is extended by being stretched to an extended, stretched, biased length.

In a subsequent step of this embodiment a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its extended, stretched and biased length. During formation of the fibrous nonwoven gatherable web the nonwoven elastic web is maintained at an extended, stretched length which is at least about 125 percent, that is at least about one and one quarter of the contracted, unbiased length of the nonwoven elastic web. For example, during formation of the fibrous nonwoven gatherable web on the extended, stretched surface of the nonwoven elastic web, the stretched, biased length of the nonwoven elastic web may be maintained in the range of from at least about 125 percent of the contracted, unbiased length of the nonwoven elastic web to about 700 or more percent of the contracted, unbiased length of the nonwoven elastic web.

Upon its formation on the surface of the nonwoven elastic web, the fibrous nonwoven gatherable web is separably joined to the nonwoven elastic web while the nonwoven elastic web is maintained at its extended stretched, biased length. This results in the formation of a composite nonwoven elastic web which includes the nonwoven elastic web and the fibrous nonwoven gatherable web with the fibrous nonwoven gatherable web being separably joined to the nonwoven elastic web. Because the fibrous nonwoven gatherable web is formed directly onto the surface of the nonwoven elastic web while the nonwoven elastic web is being maintained at its extended stretched, biased length, the nonwoven elastic web is, at this stage in the process, extended, stretched and biased and the fibrous nonwoven gatherable web is in an ungathered but gatherable condition.

The separable joining of the fibrous nonwoven gatherable web to the extended, stretched nonwoven elastic web is achieved by the entanglement of the individual fibers of the fibrous nonwoven gatherable web with the nonwoven elastic web during formation of the fibrous nonwoven gatherable web on the surface of the nonwoven elastic web. If the nonwoven elastic web is a fibrous nonwoven elastic web formed by, for example, meltblowing, the separable joining of the fibrous nonwoven gatherable web to the fibrous nonwoven elastic web is achieved by entanglement of the individual fibers of the fibrous gatherable web with the individual fibers of the fibrous nonwoven elastic web. If the nonwoven elastic web is an apertured film, the separable joining of the fibrous nonwoven web with the nonwoven elastic web is achieved by entanglement of the individual fibers of the fibrous gatherable web within the apertures of the apertured film.

After the separable joining of the two webs to each other has been achieved to form the composite elastic web, the biasing force is removed from the composite nonwoven elastic web and the composite elastic web is allowed to contract, due to contraction of the stretched nonwoven elastic web, to its normal contracted, unbiased length. Because the fibrous nonwoven gatherable web is separably joined to the nonwoven elastic web while the nonwoven elastic web is extended and stretched, contraction of the composite nonwoven elastic web results in the gatherable web being carried with the contracting nonwoven elastic web and thus being gathered on the surface of the nonwoven elastic web.

After gathering of the fibrous nonwoven gatherable web has occurred by reducing the biasing force on the composite nonwoven elastic web the gathered fibrous nonwoven web is separated from the nonwoven elastic web and the gathered web may, for example, be rolled up for storage. After separation of the fibrous nonwoven gathered web from the nonwoven elastic web, the nonwoven elastic web may be reused as a forming surface.

Upon its separation from the nonwoven elastic web, the fibrous nonwoven gathered web retains a gathered configuration and, upon application of a stretching and biasing force in the direction in which the fibrous nonwoven gatherable web was gathered, the gathered web extends to the extent that the gathers allow. Importantly, upon release of the stretching and biasing force the extended, fibrous nonwoven gathered web contracts substantially to the gathered configuration and length which it possessed after its separation from the nonwoven elastic web. That is, the fibrous nonwoven gathered web exhibits elastic characteristics and properties. The fact that the gathered web, upon its separation from the nonwoven elastic web, retains a gathered configuration is surprising. However, it is even more surprising that the separated fibrous nonwoven gathered web, upon being stretched to an extended length, exhibits elastic properties such as recovering at least about 40 percent of its elongation. That is, the separated fibrous nonwoven web exhibits elastic or elastomeric properties as defined herein. In fact, it has been found that the fibrous nonwoven gathered web exhibits these elastic properties even when the fibrous nonwoven gathered web was formed from a nonelastic material such as polypropylene.

Preferably, the fibrous nonwoven gatherable web includes at least one meltblown fibrous nonwoven web. Alternative methods which may be utilized in forming the fibrous nonwoven gatherable web include spunbonding or any other process for forming a fibrous nonwoven gatherable web. The gathered fibrous nonwoven web may be formed entirely from one nonelastic material or from a blend of one or more nonelastic materials. However, the gathered fibrous nonwoven may be formed from blends of one or more nonelastic materials with one or more elastic materials or from one or more elastic materials. Nonelastic materials for forming the fibrous nonwoven gatherable web include nonelastic polyester materials, nonelastic polyolefin materials or blends of one or more nonelastic polyester materials with one or more nonelastic polyolefin materials. An exemplary nonelastic polyester material is polyethylene terephthalate. An exemplary nonelastic polyolefin is a nonelastic polypropylene which may be obtained under the trade designation PF 301.

DESCRIPTION OF THE PREFERRED EMBODIMENTS

Figure 1:
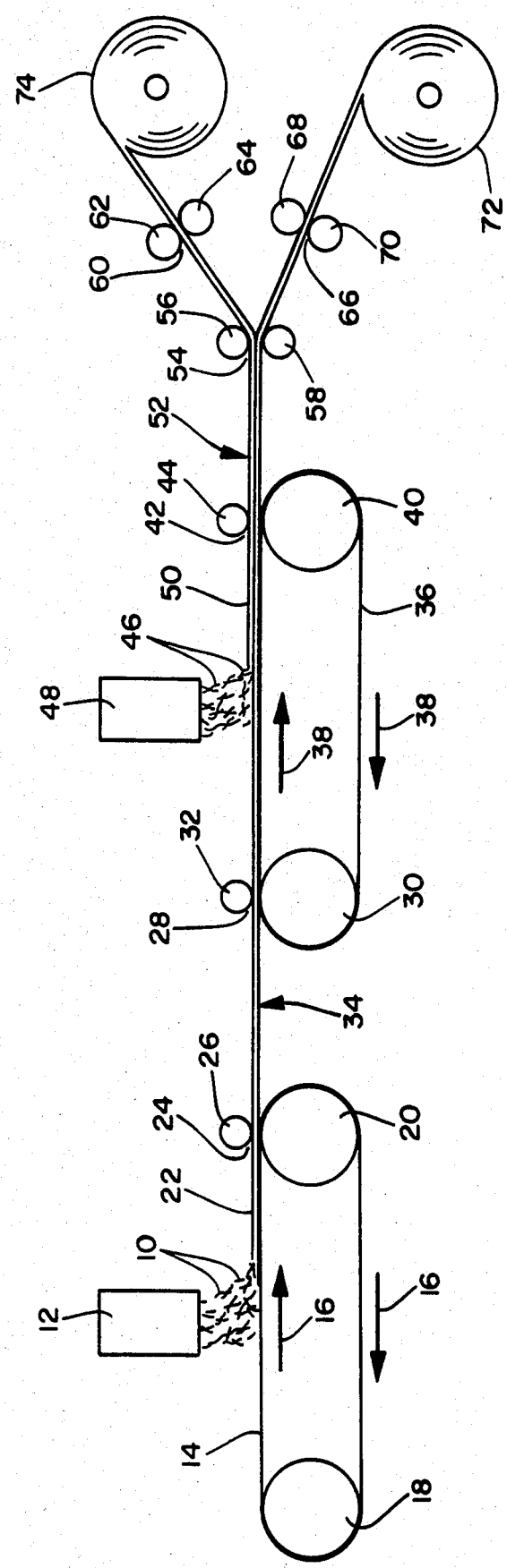
FIG. 1 is a schematic view illustrating one mode for carrying out the method of the present invention.

Turning now to the figures wherein like reference numerals represent like structure and, in particular, to FIG. 1, it can be seen that meltblown microfibers 10 which are formed by a conventional meltblowing die 12 are collected on a porous collecting screen 14 which is moving, as indicated by the arrows 16 in FIG. 1, about the rollers 18 and 20. The material which is utilized to form the meltblown microfibers 10 is, for reasons which will hereinafter become clear, an elastomeric material which will be discussed in detail hereinbelow. The porous collecting screen 14 is driven by the rotating rollers 18 and 20 which, in turn, are driven by a conventional drive arrangement (not shown). Also not shown for purposes of clarity is a conventional vacuum box located between the rollers 18 and 20 and beneath the lower surface of the upper portion of the screen 14. The vacuum box assists in the retention of the microfibers 10 on the upper surface of the screen 14. As the meltblown microfibers 10 are deposited upon the moving collecting screen 14 they entangle and cohere to form a cohesive fibrous nonwoven elastic web 22. The entangled cohesive fibrous nonwoven elastic web 22 is carried by the porous collecting screen 14 to the nip or gap 24 between the rotating roller 20 and a rotating nip roller 26. The nip or gap 24 between the two rollers 20 and 26 is adjusted so that the rollers 20 and 26 firmly engage the fibrous nonwoven elastic web 22 without adversely affecting the web 22. The rate of rotation of the rollers 20 and 26 is adjusted so that the peripheral surface speed of the rollers 20 and 26 is substantially the same as the speed of the moving porous collecting screen 14. If, upon lay-down on the surface of the porous screen 14, the meltblown microfibers 10 are insufficiently cohered to each other to form a cohesive web 22 capable of performing the hereinafter discussed extending, that is stretching, and contracting, that is relaxing, steps without being adversely affected (e.g. the web separates and loses its integrity, upon application of a stretching force), the cohesion of the microfibers 10 to each other may be improved by, for example, conventionally heat-bonding the microfibers 10 to each other by maintaining the roller 26 at an appropriate elevated temperature which will vary depending upon the degree of cohesion desired and the cohesive characteristics of the material utilized to form the microfibers 10. Typical heat-bonding temperatures range from about 50 degrees centigrade below the melting temperature of at least one of the materials utilized to form the web 22 to about the melting temperature of at least one of the materials utilized to form the web 22. However, at high throughput rates temperatures exceeding the melting temperature of the material may be employed. After passing through the nip 24 the fibrous nonwoven elastic web 22 is forwarded by the action of the rollers 20 and 26 into and passes through a second nip or gap 28 which is formed between a rotating roller 30 and a second rotating nip roller 32. Rotation of the rollers 30 and 32 is adjusted so that the peripheral surface speed of the rollers 30 and 32 is greater than the peripheral surface speed of the rollers 20 and 26. The nip 28 between the two rollers 30 and 32 is adjusted so that the rollers 30 and 32 firmly engage the fibrous nonwoven elastic web 22 without adversely affecting the web 22. As a result of the increase in the peripheral surface speed of the rollers 30 and 32 with respect to the peripheral surface speed of the rollers 20 and 26 a longitudinal or machine direction (MD) biasing force is placed on the fibrous nonwoven elastic web 22 and the web 22 is stretched to an extended, stretched, biased length in the longitudinal or machine direction (MD). The degree of stretching of the fibrous nonwoven elastic web 22 which occurs in the area 34 between the rollers 20 and 26 and the rollers 30 and 32 may be varied, for example, by varying the peripheral surface speed of the rollers 30 and 32 with respect to the peripheral surface speed of the rollers 20 and 26. For example, if the peripheral surface speed of the rollers 30 and 32 is about twice that of the rollers 20 and 26, the fibrous nonwoven elastic web 22 will be stretched to a stretched and extended length of substantially about twice, that is, about 200 percent, of its relaxed, contracted, unstretched and unbiased length. It is preferred that the fibrous nonwoven web 22 be stretched or extended to a stretched or extended length of at least about 125 percent of its relaxed, contracted and unbiased length, that is, elongated at least about 25 percent. In particular, it is preferred for the fibrous nonwoven web 22 to be stretched to a stretched or extended length of from at least about 125 percent of the relaxed, unbiased, contracted length of the fibrous nonwoven elastic web 22 to about 700 or more percent of the relaxed, unbiased and contracted length of the fibrous nonwoven elastic web 22.

After the fibrous nonwoven elastic web 22 has been stretched by the combined actions of rollers 20 and 26 and 30 and 32, the web 22 is passed onto a second porous collecting screen 36 which is moving as is indicated by the arrows 38 in FIG. 1. The second porous collecting screen 36 moves about and is driven by the rotating roller 30 in conjunction with a rotating roller 40. The rotating rollers 30 and 40 are, in turn, driven by a conventional driving arrangement (not shown) which may be the same arrangement that is driving the rotating rollers 18 and 20. Also not shown for purposes of clarity is a conventional vacuum box located between the rollers 30 and 40 and beneath the lower surface of the upper portion of the screen 36. The vacuum box assists in the retention of the web 22 on the upper surface of the screen 36. The stretched fibrous nonwoven elastic web 22 is carried by the second porous collecting screen 36 to a nip or gap 42 which is formed between the rotating roller 40 and a third rotating nip roller 44. Rotation of the rotating roller 40 and the rotating nip roller 44 is adjusted so that the peripheral surface speed of the two rollers 40 and 44 is substantially the same as the peripheral surface speed of the rollers 30 and 32. Because the peripheral surface speed of the rollers 40 and 44 is maintained at substantially the same peripheral surface speed as that of the rollers 30 and 32 and because the nip 42 is adjusted so that the rollers 40 and 44 firmly retain the fibrous nonwoven elastic web 22, without adversely affecting the web 22, the stretched and extended condition of the fibrous nonwoven elastic web 22 is maintained while the fibrous nonwoven elastic web 22 is being carried by the second porous collecting screen 36.

While the stretched, extended fibrous nonwoven elastic web 22 is being carried by the second porous collecting screen 36, meltblown microfibers 46, formed by a conventional meltblowing die 48, are meltblown directly onto the upper surface of the stretched nonwoven elastic web 22 to form a cohesive fibrous nonwoven gatherable web 50 which is located on the upper surface of the stretched fibrous nonwoven elastic web 22. Care should be taken to adjust the distance between the die tip of the meltblowing die 48 and the elastic web 22 and the speed at which the elastic web 22 passes under the die tip of the meltblowing die 48 as it has been found that the hot air exiting the die tip will melt the elastic web 22 if the adjustments, which will vary with the material or blend of materials from which the elastic web 22 is formed, are not properly made. As the meltblown microfibers 46 are collected on the upper surface of the fibrous nonwoven elastic web 22, they entangle and cohere with each other to form the cohesive fibrous nonwoven gatherable web 50. Depending upon the distance between the die tip of the meltblowing die 48 and the upper surface of the stretched fibrous nonwoven elastic web 22 the meltblown microfibers 46 may also mechanically entangle with the fibers of the elastic web 22. Generally speaking, as the distance between the die tip of the meltblowing die 48 and the upper surface of the stretched firbrous nonwoven web 22 is increased the mechanical entanglement of the fibers of the web 50 with the fibers of the web 22 decreases. To assure mechanical entanglement of the fibers of the web 50 with the fibers of the web 22 the distance between the die tip of the meltblowing die 48 and the upper surface of the web 22 should be no greater than about 25 inches. Preferably, the distance between the die tip of the meltblowing die 48 and the upper surface of the web 22 should range from about 6 inches to about 16 inches. Depending on the materials utilized to form the webs 22 and 50 and the distance between the die tip of the meltblowing die 48 and the upper surface of the elastic web 22 some adhesion of the fibers of the gatherable web 50 to the fibers of the elastic web 22 may also occur. The elastomeric materials which are appropriate for utilization in forming the fibrous nonwoven elastic web 22 are preferably selected after selection of the material or materials which will be utilized in formation of the fibrous nonwoven gatherable web 50 has occurred. In particular, the material selected to form the fibrous nonwoven gatherable web 50 must be a material which forms a web 50 that is gatherable by the contracting and relaxing force of the fibrous nonwoven elastic web 22. Because the contacting and relaxing force of the web 22 will vary with the material or materials selected for formation of the web 22, the material or materials selected for formation of the web 22 will have to be selected so that the contracting force of the web 22 is capable of gathering the web 50. Exemplary materials for utilization in forming the webs 22 and 50 are disclosed hereinafter.

Because the fibrous nonwoven gatherable web 50 will be separated from the nonwoven elastic web in a later step, a relatively weak and separable joining of the two webs 22 and 50 to each other is required. This weak and separable joining of the two webs 22 and 50 to each other is achieved by the entanglement of the individual fibers of the fibrous nonwoven gatherable web 50 with the individual meltblown fibers of the fibrous nonwoven elastic web 22 which occurs during formation of the web 50 on the stretched surface of the web 22. Therefore, the two webs 22 and 50 are separable from each other upon application of a relatively small amount of force such as, for example, a light picking force applied by an individual's fingers.

After the fibrous nonwoven elastic web 22 has been separably joined to the fibrous nonwoven gatherable web 50 to form a composite nonwoven elastic web 52 the biasing force on the fibrous nonwoven elastic web 22 is relaxed by, for example, passing the composite nonwoven elastic web 52, which includes the separably joined fibrous nonwoven elastic and fibrous nonwoven gatherable webs 22 and 50, through the nip or gap 54 formed by a pair of rotating nip rollers 56 and 58. The nip 54 is adjusted so that the rollers 56 and 58 firmly engage the composite web 52 without adversely affecting the composite web 52. The rotation of the pair of nip rollers 56 and 58 is adjusted so that the peripheral surface speed of the nip rollers 56 and 58 allows the composite nonwoven elastic web 52 to relax and, as a result of the elastic properties of the fibrous nonwoven elastic web 22, to contract to its contracted, unbiased length. The relaxing and contracting of the composite nonwoven elastic web 52 to its relaxed, contracted unbiased length results in the fibrous nonwoven gatherable web 50 being carried along with the contracting web 22 and thus gathered upon the upper surface of the contracting fibrous nonwoven elastic web 22.

After relaxing and contracting of the composite nonwoven elastic web 52 and gathering of the fibrous nonwoven gatherable web 50 has occurred, the two webs 22 and 50 are separated from each other by being lightly pulled apart. The separation of the two webs 22 and 50 from each other is effected in this embodiment by passing the fibrous nonwoven gathered web 50 through the nip 60 between two rotating nip rollers 62 and 64 and passing the nonwoven elastic web 22 through the nip 66 between two rotating nip rollers 68 and 70. The nips 60 and 66 are adjusted so that the rollers 62 and 64 engage the web 50 without adversely affecting the web 50 and the rollers 68 and 70 engage the web 22 without adversely affecting the web 22. After separation of the two webs 22 and 50, the two webs 22 and 50 are wound up on storage rolls 72 and 74, respectively. Care should be taken in winding up the fibrous nonwoven gathered web 50 so that the web 50 is not stored under high tension or biasing in an ungathered condition because, if the web 50 is stored in a rolled-up tensioned, ungathered condition it is believed that the web 50 will lose its ability to retain its gathers. Loss of the gathers in the web 50 will result in a loss of the elastic characteristics of the web 50. Accordingly, in order to retain the gathered condition of the web 50 while the web 50 is stored the rotation of the storage roll 74 should be adjusted so that the peripheral surface speed of the roll 74 is generally equal to or just slightly greater than the peripheral surface speed of the rollers 62 and 64.

Upon its separation from the nonwoven elastic web 22 the gathered fibrous nonwoven web 50 exhibits a creped or gathered appearance. Upon application of an extending force in the machine direction (i.e. is a direction substantially perpendicular to the lines of gathering) the web 50 is extended to the extent that the gathers allow, e.g. until the web 50 has assumed a generally planar configuration as opposed to a gathered configuration and, surprisingly, upon release of the extending force on the gathers, the gathered web 50 exhibits elastic characteristics as defined herein. The gathered web 50 exhibits elastic characteristics even when the web 50 was formed from a nonelastic material such as a polypropylene obtained from the Himont Corporation under the trade designation PF 301.

The fibrous nonwoven elastic web 22 portion of the composite nonwoven elastic web 52 may be formed from any elastomeric material which may be formed into a fibrous nonwoven elastic web 22. Exemplary elastomeric materials for use in formation of the fibrous nonwoven elastic web 22 include polyester elastomeric materials such as, for example, polyester elastomeric materials available under the trade designation Hytrel from E. I. DuPont DeNemours & Co., polyurethane elastomeric materials such as, for example, polyurethane elastomeric materials available under the trade designation Estane from B. F. Goodrich & Co. and polyamide elastomeric materials such as, for example, polyamide elastomeric materials available under the trade designation Pebax from the Rilsan Company. Other elastomeric materials for use in forming the fibrous nonwoven elastic web 22 include (a) A-B-A' block copolymers, where A and A' are each a thermoplastic polymer endblock containing a styrenic moiety and where A may be the same thermoplastic polymer endblock as A', for example, a poly (vinyl arene), and where B is an elastomeric polymer midblock such as conjugated diene or a lower alkene or (b) blends of one or more polyolefins or poly (alpha-methylstyrene) with the elastomeric A-B-A' block copolymer material, where A and A' are each a thermoplastic endblock containing a styrenic moiety and where A may be the same thermoplastic polymer endblock as A', such as a poly (vinyl arene) and where B is an elastomeric polymer midblock, such as a conjugated diene or a lower alkene. The A and A' materials may each be selected from the group of materials including polystyrene or polystyrene homologs and B may be selected from the group of materials including polyisoprene, polybutadiene and poly (ethylene-butylene). Materials of this type are disclosed in U.S. Pat. Nos. 4,323,534 to Des Marais and 4,355,425 to Jones and in the aforementioned Shell brochure. Commercially available elastomeric A-B-A' block copolymers having a saturated or essentially saturated poly (ethylene-butylene) midblock "B" represented by the formula:

poly(ethylene-butylene)

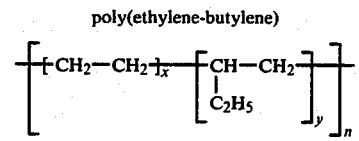

where x, y and n are positive integers and polystyrene end blocks A and A' represented by the formula:

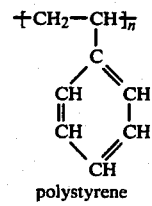

polystyrene where n is a positive integer which may be the same or different integer for A and A', are sometimes referred to as S-EB-S block copolymers and are available under the trade designation KRATON G; for example, KRATON G 1650, KRATON G 1652 and KRATON GX 1657 from the Shell Chemical Company. Other elastomeric resins which may be utilized are A-B-A' block copolymers where A and A' are each a polystyrene endblock as defined above and "B" is a polybutadiene midblock represented by the following formula:

polybutadiene

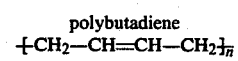

where n is a positive integer. This materials are sometimes referred to as a S-B-S block copolymers and are available under the trade designation KRATON D; for example, KRATON D 1101, KRATON D 1102 and KRATON D 1116, from the Shell Chemical Company. Another S-B-S block copolymer material may be obtained under the trade designation Solprene 418 from the Phillips Petroleum Company. Yet another elastomeric resins which may be utilized are A-B-A' block copolymers where A and A' are each polystyrene endblocks, as defined above, and "B" is a polyisoprene midblock represented by the formula:

polyisoprene

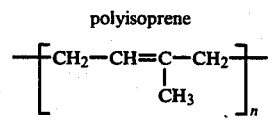

where n is a positive integer. These block copolymers are sometimes referred to as S-I-S block copolymers and are available under the trade designation KRATON D; for example, KRATON D 1107, KRATON D 1111, KRATON D 1112 and KRATON D 1117, from the Shell Chemical Company.

A summary of the typical properties of the above-identified KRATON D and KRATON G resins at 74 degrees Fahrenheit is presented below in Tables I and II.

TABLE I

| PROPERTY | KRATON D | | | | | | |
|---|---|---|---|---|---|---|---|
| | D-1101 | D-1102 | D-1107 | D-1111 | D-1112 | D-1116 | D-1117 |
| Tensile Strength, psi[1] | 4,600[2] | 4,600[2] | 3,100[2] | 2,900[2] | 1,500[2] | 4,600[5] | 1,200[2] |
| 300% Modulus, psi[1] | 400 | 400 | 100 | 200 | 70 | 350 | 60 |
| Elongation, %[1] | 880 | 880 | 1,300 | 1,200 | 1,400 | 900 | 1,300 |
| Set at Break, % | 10 | 10 | 10 | 10 | 20 | 10 | 15 |
| Hardness, Shore A | 71 | 71 | 37 | 52 | 34 | 65 | 32 |
| Specific Gravity | 0.94 | 0.94 | 0.92 | 0.93 | 0.92 | 0.94 | 0.92 |
| Brookfield Viscosity, (Toluene Solution) cps at 77° F. | 4,000[3] | 1,200[3] | 1,600[3] | 1,300[3] | 900[3] | 9,000[3] | 500[3] |
| Melt Viscosity Melt Index, Condition G, gms/10 min. | 1 | 6 | 9 | — | — | — | — |
| Plasticizer Oil Content, % w | 0 | 0 | 0 | 0 | 0 | 0 | 0 |
| Styrene/6 Rubber Ratio | 31/69 | 28/72 | 14/86 | 21/79 | 14/86 | 21/79 | 17/83 |
| Physical Form | Porous Pellet | Porous Pellet | Pellet | Porous Pellet | Pellet | Porous Pellet | Pellet |

TABLE II

| PROPERTY | KRATON G | | |
|---|---|---|---|
| | G-1650 | G-1652 | GX-1657 |
| Tensile Strength, psi[1] | 5,000[2] | 4,500[2] | 3,400[2] |
| 300% Modulus, psi[1] | 800 | 700 | 350 |
| Elongation, %[1] | 500 | 500 | 750 |
| Set at Break, % | — | — | — |
| Hardness, Shore A | 75 | 75 | 65 |
| Specific Gravity | 0.91 | 0.91 | 0.90 |
| Brookfield Viscosity, (Toluene Solution) cps at 77° F. | 1,500[4] | 550[4] | 1,200[4] |
| Melt Viscosity, Melt Index, Condition G, gms/10 min. | — | — | — |
| Plasticizer Oil Content, % w | 0 | 0 | 0 |
| Styrene/Rubber[6] Ratio | 28/72 | 29/71 | 14/86 |
| Physical Form | Crumb | Crumb | Pellet |

[1]ASTM method D412-tensile test jaw separation speed 10 in./min.
[2]Typical properties determined on film cast from a toluene solution.
[3]Neat polymer concentration, 25% w.
[4]Neat polymer concentration, 20% w.
[5]Property determined by extrapolation to zero oil content of results measured on oil extended films cast from toluene solution.
[6]The ratio of the sum of the molecular weights of the endblocks (A + A') to the molecular weight of the B midblock. For example, with respect to KRATON G-1650, the sum of the molecular weights of the endblocks (A + A') is 28 percent of the molecular weight of the A-B-A' tri-block copolymer.

Meltblowing of the pure, i.e. neat, S-EB-S KRATON G block copolymers has proven to be quite difficult except at elevated temperatures and low through-puts such as from at least about 550 degrees Fahrenheit to about 625 degrees Fahrenheit or more and below at least about 0.14 grams per die capillary per minute. In order to avoid these elevated temperatures and low through-put conditions, blending of certain materials with several of the different types of KRATON G materials has proven to provide a satisfactory meltblowable material. For example, blends of certain polyolefin materials with the KRATON G S-EB-S block copolymers has resulted in a meltblowable material. In particular, if a polyolefin is blended with a S-EB-S block copolymer, the polyolefin is preferably a polymer, including copolymers, of ethylene, propylene, butene, other lower alkenes or blending one or more of these materials. A preferred polyolefin for blending with the KRATON G S-EB-S block copolymers is polyethylene and a preferred polyethylene may be obtained from the U.S.I. Chemical Company under the trade designation Petrothene Na601. (Also referred to as PE Na601 or Na601.)

Information obtained from U.S.I. Chemical Company states that the Na601 is a low molecular weight, low density polyethylene for application in the areas of hot melt adhesives and coatings. U.S.I. has also stated that the Na601 has the following nominal values: (1) a Brookfield Viscosity, cP at 150 degrees Centigrade of 8500 and at 190 degrees Centigrade of 3300 when measured in accordance with ASTM D 3236; (2) a density of 0.903 grams per cubic centimeter when measured in accordance with ASTM D 1050; (3) an equivalent Melt index of 2000 grams per ten minutes when measured in accordance with ASTM D 1238; (4) a ring and ball softening point of 102 degrees Centigrade when measured in accordance with ASTM E 28; (5) a tensile of 850 pounds per square inch when measured in accordance with ASTM D 638; (7) a modulus of Rigidity, $T_F$ (45,000) of −34 degrees Centigrade and (8) a penetration Hardness, (tenths of mm) at 77 degrees Fahrenheit of 3.6.

The Na601 is believed to have a number average molecular weight (Mn) of about 4,600; a weight average molecular weight (Mw) of about 22,400 and a Z average molecular weight (Mz) of about 83,300. The polydisperisity of the Na601 (Mw/Mn) is about 4.87.

Mn is calculated by the formula:

$$Mn = \frac{\text{Sum }[(n)(MW)]}{\text{Sum }(n)}$$

and Mw is calculated by the formula:

$$Mw = \frac{\text{Sum }[(n)(MW)^2]}{\text{Sum }[(n)(MW)]}$$

and Mz is calculated by the formula:

$$Mz = \frac{\text{Sum }[(n)(MW)^3]}{\text{Sum }[(n)(MW)^2]}$$

where:
MW = The various molecular weights of the individual molecules in a sample, and
n = The number of molecules in the given sample which have a given molecular weight of MW.

Blending polyolefin materials with the KRATON S-B-S and S-I-S block copolymers followed by meltblowing of the blend has, to date, proven unsatisfactory in that the blends appear to be incompatible. However, blending of poly (alpha-methylstyrene) with the S-I-S block copolymers has resulted in a meltblowable material. A preferred poly (alpha-methylstyrene) may be obtained from Amoco under the trade designation 18-210.

The gathered fibrous nonwoven elastic web 50 formed by the process of the present invention may be formed from any gatherable material which may be formed into a fibrous nonwoven web 50 and which will substantially retain a gathered condition upon separation of the web 50 from the web 22. It is presently believed that, in most embodiments, the gathered condition (e.g. configuration) which the fibrous nonwoven gatherable web 50 exhibits upon its separation from the web 22 will be somewhat longer in the direction of gathering (i.e. machine direction) as compared to the length of the same amount of web 50 when the web 50 is separably joined to the elastic web 22. In other words, the web 50 will extend somewhat in the direction of gathering after its separation from the web 22. Accordingly, the gathered, relaxed, unbiased length of the separated web 50 will be somewhat greater than or equal to the gathered, relaxed, unbiased length of the same amount of the web 50 while it is joined to the elastic web 22.

Preferably, the gathered fibrous nonwoven web 50 is formed solely from one or more nonelastic materials. However, the gathered fibrous nonwoven web 50 could be formed from a blend of a nonelastic material with an elastic material, one or more elastic materials or a blend of two or more elastic materials with two or more nonelastic materials. Preferably, the gathered fibrous nonwoven elastic web 50 is formed solely from one or more fiber-forming meltblowable or spunbondable nonelastic gatherable materials. Exemplary nonelastic fiber-forming materials for use in forming the gathered fibrous nonwoven elastic web are nonelastic polyester materials, nonelastic polyolefin materials or blends of one or more nonelastic polyester materials with one or more nonelastic polyolefin materials. An exemplary nonelastic polyester fiber-forming material is polyethylene terephthalate. Examplary nonelastic fiber-forming polyolefin materials are polypropylenes which may be obtained under the trade designations PC 973 and PF 301 from the Himont Company.

Typical characteristics of the Himont PC-973 polypropylene stated by Himont are a density of about 0.900 grams per cubic centimeter measured in accordance with ASTM D 792; a melt flow rate of about 35 grams per ten minutes measured in accordance with ASTM D 1238, condition L; tensile of about 4,300 pounds per square inch (psi) measured in accordance with ASTM D 638; flex modulus of about 182,000 psi measured in accordance with ASTM D 790, B and a Rockwell hardness, R scale, of about 93 measured in accordance with ASTM D 785A. The PC-973 is believed to have a number average molecular weight (Mn) of about 40,100; a weight average (Mw) molecular weight of about 172,000 and a Z average molecular weight of about 674,000. The polydispersity (Mw/Mn) of the PC-973 is about 4.29.

Figure 2:
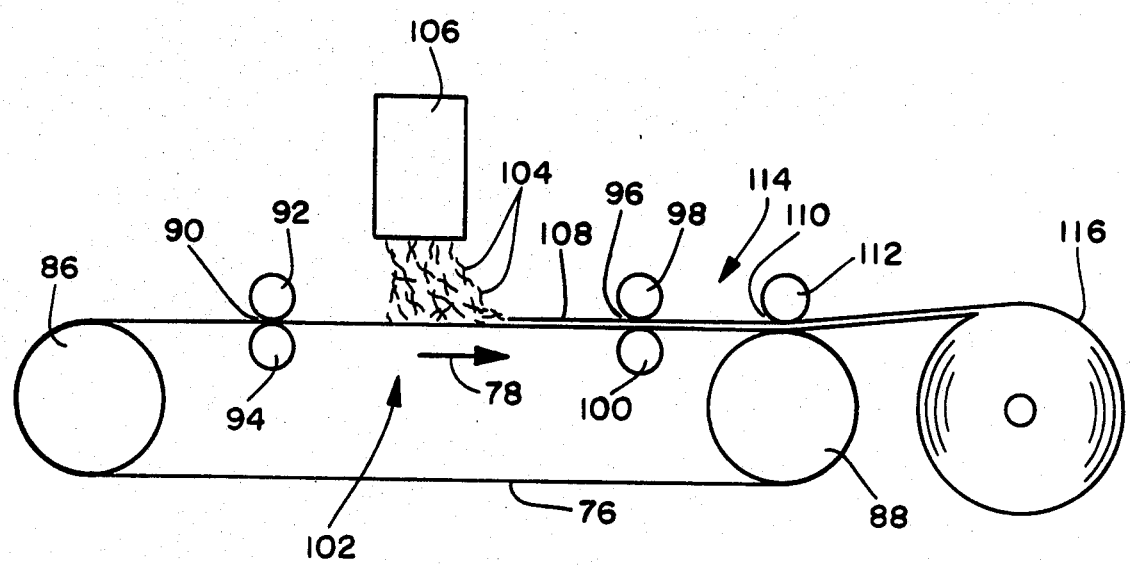
FIG. 2 is a schematic view illustrating another mode for carrying out the method of the present invention.
Figure 3:
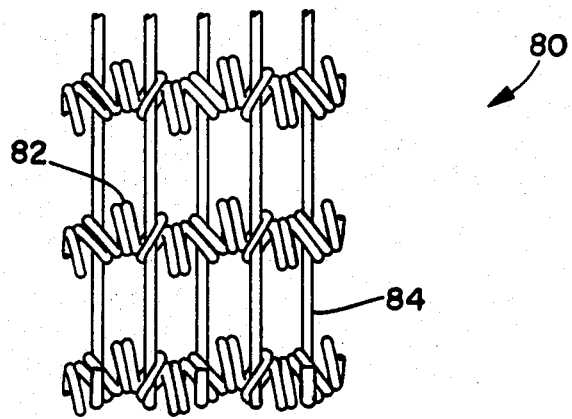
FIG. 3 is a top plan view of an unbiased and retracted extendable and retractable forming screen which may be utilized as a forming screen in the process illustrated in FIG. 2.
Figure 4:
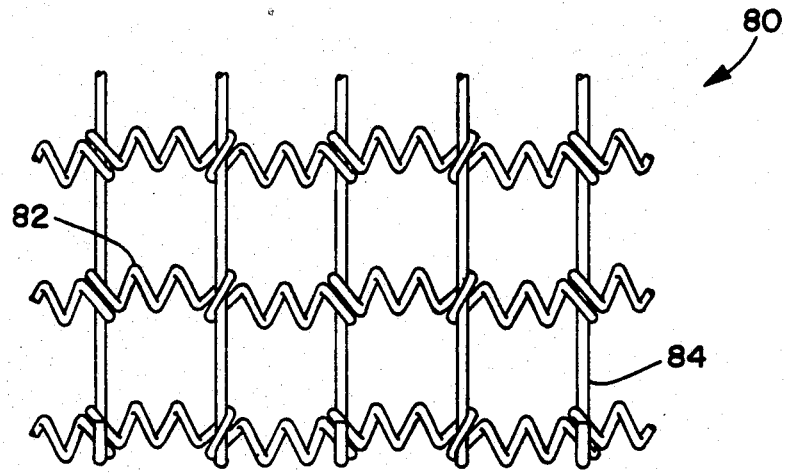
FIG. 4 is a top plan view of the extendable and retractable forming screen of FIG. 3 in the biased, extended configuration.

FIG. 2 illustrates another embodiment of the present invention which avoids the requirement of forming the gathered nonwoven elastic web 50 of the embodiment of FIG. 1 on the stretched, extended surface of the nonwoven elastic web 22. In the embodiment of FIG. 2 the gathered nonwoven elastic web 50 is formed directly on the surface of a porous forming screen 76 which, itself, is extendable and retractable in the machine direction of movement as is indicated by the arrow 78. For example, the extendable and retractable porous collecting screen 76 could be formed from a continuous web of the nonwoven elastic web 22. Alternatively, the extendable and retractable porous collecting screen 76 could be formed from a wire mesh screen 80 which is generally illustrated in FIG. 3. The wire mesh screen 80 could be formed from a plurality of substantially parallel springs 82 coiled and extending in the machine direction (MD) with the springs 82 being connected to each other in the transverse machine direction (TD) by a plurality of fine, generally parallel wires 84 extending in the transverse machine direction (TD). The transverse direction wires 84 may be arranged very closely to each other so that, when the wire mesh 80 is in an unbiased, retracted or contracted configuration, the transverse direction wires 84 contact each other. Upon application of a tensioning or biasing force in the machine direction, the coiled springs 82 will extend, that is, stretch, in the machine direction and the fine transverse direction wires 84 will separate from each other to form the porous collecting surface 76. This biased, stretched, extended configuration is generally illustrated in FIG. 4. Alternatively, the wire mesh screen 30 could be formed by a plurality of substantially parallel springs coiled and extending in the transverse machine direction (TD) with the springs being connected to each other in the machine direction (MD) by a plurality of fine, generally parallel wires extending in the machine direction (MD). This configuration would be illustrated upon rotating FIGS. 3 and 4 90° and results in a configuration by which the gatherable web 108 could be gathered in the transverse machine direction (TD) as opposed to the machine direction (MD) as is illustrated in the figures. If gathering of the gatherable web 108 in the transverse direction is desired additional conventional arrangements (not shown) for extending and contracting the screen 80 in the transverse direction would replace the arrangement illustrated in the figures for extending and contracting the screen 80 in the machine direction (MD).

Returning to FIG. 2 it can be seen that movement of the extendable and retractable porous collecting screen 76 in the machine direction 78 is accomplished by the screen 76 being driven by rollers 86 and 88 which are, in turn, driven by conventional drive mechanism (not shown). Also not shown for purposes of clarity is a conventional vacuum box located between the rollers 86 and 88 and beneath the lower surface of the upper portion of the screen 76. The vacuum box assists in the retention of the web 22 on the upper surface of the screen 76. The extendable and contractable porous collecting screen 76 passes through the nip 90 between a pair of rotating nip rollers 92 and 94. The nip 90 is adjusted so that the rollers 92 and 94 firmly engage the extendable and retractable or contractable porous collecting screen 76 without adversely affecting the screen 76. Rotation of the rollers 92 and 94 is adjusted so that the peripheral surface speed of the rollers 92 and 94 is substantially the same as the peripheral surface speed of the rollers 86 and 88. The extendable and retractable or contractable porous collecting screen 76 also passes through the nip 96 between another pair of rotating nip rollers 98 and 100 with the nip 96 being adjusted so that the rollers 98 and 100 firmly engage the porous collecting screen 76 without adversely affecting the porous collecting screen 76. The rotation of the rollers 98 and 100 is adjusted so that the peripheral surface speed of the rollers 98 and 100 is greater than the peripheral surface speed of the rollers 92 and 94. As a result of the increase in the peripheral surface speed of the rollers 98 and 100 with respect to the peripheral surface speed of the rollers 92 and 94 a longitudinal or machine direction (MD) biasing and extending force is placed on the extendable and contractable porous collecting screen 76 and the screen 76 is extended to an extended, biased length in the longitudinal direction in the area 102. The degree of extension of the porous collecting screen 76 which occurs in the area 102 between the rollers 92 and 94 and the rollers 98 and 100 may be varied, for example, by varying the peripheral surface speed of the rollers 98 and 100 with respect to the peripheral surface speed of the rollers 92 and 94. For example, if the peripheral surface speed of the rollers 98 and 100 is about twice that of the rollers 92 and 94, the extendable and retractable porous collecting screen 76 will be extended to an extended, biased length of substantially about twice, that is, about 200 percent, of its retracted, unbiased length. It is preferred for the extendible and retractable porous collecting screen 76 to be extended, in the area 102, to a length which is at least about 150 percent of its contracted, unbiased and unextended length. In particular, it is preferred for the screen 76 to be extended to an extended length, in the area 102, of from at least about 150 percent of its retracted, unbiased and unextended length. More particularly, it is preferred for the porous collecting surface 76 to be extended to an extended length of from at least about 150 percent of the retracted, unbiased and unextended length of the porous collecting surface 76 to about 700 or more percent of the retracted, unbiased and unextended length of the porous collecting surface 76.

While the extendable and retractable porous collecting screen 76 is in the extended configuration in the area 102, meltblown microfibers 104, which are formed by a conventional meltblowing die 106 are meltblown onto the extended surface of the porous collecting screen 76. As the meltblown microfibers 104 are deposited upon the extended porous collecting screen 76 they entangle and cohere to form a cohesive fibrous nonwoven gatherable web 108. The entangled cohesive fibrous nonwoven gatherable web 108 is carried by the porous collecting screen 76 through the nip 96 and on to a nip 110 formed between the rotating roller 88 and a rotating nip roller 112. The peripheral surface speed of the rotating nip roller 112 is adjusted so that it is substantially the same as the peripheral surface speed of the rotating roller 88 and the rollers 86 and 92 and 94. Because the peripheral surface speed of the rollers 88 and 112 is substantially the same as the peripheral surface speed of the rollers 86 and 92 and 94 the extending force is removed from the extended porous collecting screen 76 and the screen 76 is retracted, that is allowed to contract, as a result of its contractable properties, to its contracted, unbiased length. The relaxing and contracting of the porous collecting screen 76 to its contracted, unbiased length results in the fibrous nonwoven gatherable web 108, which was formed on the surface of the screen 76 while the screen 76 was being maintained in its extended configuration, being carried along with, and retracted and thus gathered upon the upper surface of the retracting porous collecting screen 76. The gathering of the fibrous nonwoven gatherable web 108, accordingly, occurs in the area 114 between the pairs of rollers 98 and 100 and 88 and 112.

After retracting and contracting of the porous collecting screen 76, the fibrous nonwoven gatherable web 108 may be rolled up on a supply roller 116 for storage and shipment. For the reasons stated earlier the rate of rotation of the supply roller 116 should be controlled so that the gathered fibrous nonwoven 108 is stored in substantially an untensioned state. This may be accomplished by adjusting the rate of rotation of the roller 116 so that the peripheral surface speed of the roller 116 is substantially equal to or just slightly greater than the peripheral surface speed of the rollers 18 and 112.

EXAMPLE I

A fibrous nonwoven elastic web which had previously been formed by meltblowing a blend of 60 percent, by weight, of an A-B-A' block copolymer having polystyrene "A" and "A'" endblocks and a poly (ethylene-butylene) "B" midblock (obtained from the Shell Chemical Company under the trade designation KRATON GX 1657) and 40 percent, by weight, of a polyethylene (obtained from U.S.I. Chemical Company under the trade designation PE Na601) was provided in rolled-up form.

The prior meltblowing of the fibrous nonwoven elastic web was accomplished by extruding the blend of materials through a meltblowing die having thirty extrusion capillaries per lineal inch of die tip. The capillaries had a diameter of about 0.0145 inches and a length of about 0.113 inches. The blend was extruded through the capillaries at a rate of about 0.50 grams per capillary per minute at a temperature of about 570 degrees Fahrenheit. The extrusion pressure exerted upon the blend was measured as 144 pounds per square inch, gage in the capillaries. However, it is presently believed that this measurement was inaccurate due to a faulty pressure probe. The die tip configuration was adjusted so that it was recessed about 0.110 inches from the plane of the external surface of the air plates which form the forming air gaps on either side of the capillaries. The air plates were adjusted so that the two forming air gaps, one on each side of the extrusion capillaries, formed air gaps of about 0.110 inches. Forming air for meltblowing the blend was supplied to the air gaps at a temperature of about 614 degrees Fahrenheit and at a pressure of about 4 pounds per square inch, gage. The meltblown microfibers thus formed were formed onto a forming screen which is believed to have been about 16 inches from the die tip. However, measurement of this distance was not actually taken.

Later, the previously formed fibrous nonwoven elastic web was unrolled and stretched by applying a tensioning, i.e. biasing, force in the machine direction (MD) and a fibrous nonwoven gatherable web was formed on the surface of the elastic web by meltblowing polypropylene (obtained from the Himont Company under the trade designation PF 301) as microfibers onto the upper surface of the fibrous nonwoven elastic web while the fibrous nonwoven elastic web was maintained at its stretched length.

Meltblowing of the fibrous nonwoven gatherable polypropylene web was accomplished by extruding the polypropylene through a meltblowing die having 30 extrusion capillaries per lineal inch of die tip. The capillaries each had a diameter of about 0.0145 inches and a length of about 0.113 inches. The polypropylene was extruded through the capillaries at a rate of about 0.75 grams per capillary per minute and at a temperature of about 590 degrees Fahrenheit. The extrusion pressure exerted upon the polypropylene was measured as about 186 pounds per square inch, gage in the capillaries. The die tip configuration was adjusted so that it extended about 0.010 inches beyond the plane of the external surface of the air plates which form the forming air gaps on either side of the capillaries. The air plates were adjusted so that the two forming air gaps, one on each side of the extrusion capillaries, formed air gaps of about 0.018 inches. Forming air for meltblowing the polypropylene was supplied to the air gaps at a temperature of about 600 degrees Fahrenheit and at a pressure of about 2 pounds per square inch, gage. The distance between the die tip and the surface of the fibrous nonwoven elastic web upon which the gatherable polypropylene web was formed was approximately 10 inches. Because of these processing conditions, the viscosity of the polypropylene was about 124 poise and relatively large diameter polypropylene microfibers were formed on the surface of the stretched fibrous nonwoven elastic web.

Next, the tensioning, biasing force was reduced so as to allow the fibrous nonwoven elastic web to contract and for the meltblown polypropylene web to thus be gathered in the machine direction. The composite nonwoven elastic web which was formed had inter-layer integrity which, apparently, resulted from the entanglement of the individual fibers of the two webs with each other since the webs were not otherwise joined by adhesives or heat-bonding.

Upon observation of the relaxed, contracted composite nonwoven elastic web it was seen that the meltblown polypropylene web presented a creped, gathered, appearance with the lines of creping or gathering being generally transverse to the direction in which the fibrous nonwoven elastic web was stretched during formation of the meltblown polypropylene web on the surface of the fibrous nonwoven elastic web (i.e. transverse to the machine direction). Interestingly, it was also observed that the fibrous nonwoven elastic web of the contracted and relaxed composite nonwoven elastic web exhibited lines of creping or gathering which were generally parallel to the direction of stretching of the fibrous nonwoven elastic web during formation of the meltblown polypropylene included on the surface thereof (i.e. the lines of creping or gathering of the fibrous nonwoven elastic web were generally parallel to the machine direction). Accordingly, the two webbed composite included webs having transposed lines of gathering or creping which generally crossed each other generally at right angles. Formation of the lines of gathering or creping in the gathered fibrous nonwoven polypropylene web would be expected in view of the gathering of that web in the machine direction. However, formation of lines of gathering or creping in the fibrous nonwoven elastic web and, in particular, formation of lines of gathering or creping in the fibrous nonwoven elastic which are generally at right angles with the lines gathering or creping of the fibrous nonwoven gatherable polypropylene webs was unexpected.

A portion of the composite nonwoven elastic web having an approximate machine direction (MD) length of about 5 and ⅜ inches and an approximate transverse direction (TD) dimension of about 4½ inches was cut off of the composite nonwoven elastic web and the gathered fibrous nonwoven meltblown polypropylene web was separated from the fibrous nonwoven elastic web. After the gathered fibrous nonwoven meltblown polypropylene web had been separated from the fibrous nonwoven elastic web it was observed that the gathered fibrous nonwoven meltblown polypropylene web assumed a relaxed machine direction dimension of about 7 inches and retained its cross-direction dimension of about 4½ inches. Importantly, the fibrous nonwoven gathered web substantially retained its creped or gathered configuration in the machine direction. Moreover, the separated gathered polypropylene web could be elongated in the machine direction upon application of a tensioning and biasing force in the machine direction and would, upon removal of the tensioning and biasing force, return, that is, contract, substantially to its relaxed and unbiased and untensioned gathered dimension (7 inches by 4½ inches). For example, upon elongation of the 7 inch by 4½ inch sample of gathered fibrous nonwoven polypropylene web in the machine direction (MD) to an extent where the gathers had been substantially straightened out, the sample was measured and found to have a machine direction (MD) length of about 9½ inches and a transverse direction (TD) dimension of about 4½ inches. When the elongating, biasing force was removed from the sample it returned to a machine direction (MD) dimension of just over seven inches and a transverse direction (TD) dimension of about 4½ inches within one minute. Upon repetition of the elongation procedure, the sample assumed a machine direction (MD) dimension of about 9½ inches and a transverse direction (TD) dimension of about 4½ inches. Upon termination of the second elongating and stretching force, the polypropylene web assumed a machine direction (MD) dimension of about 7 1/16 inches and a transverse direction (TD) dimension of about 4½ inches within one minute. This result was unexpected since the PF 301 polypropylene was not believed to possess elastic properties.

Other variations of the present inventive process and the product formed by the process are possible. For example, a fibrous nonwoven gatherable web 50 could be separably joined to both surfaces of the fibrous nonwoven elastic web 22 to form a composite nonwoven elastic web having the following three web sequence: gathered fibrous nonwoven web/gathered fibrous nonwoven elastic web/fibrous nonwoven web with the two outer gathered webs thereafter being separated from the fibrous nonwoven elastic web 22.

Figure 5:
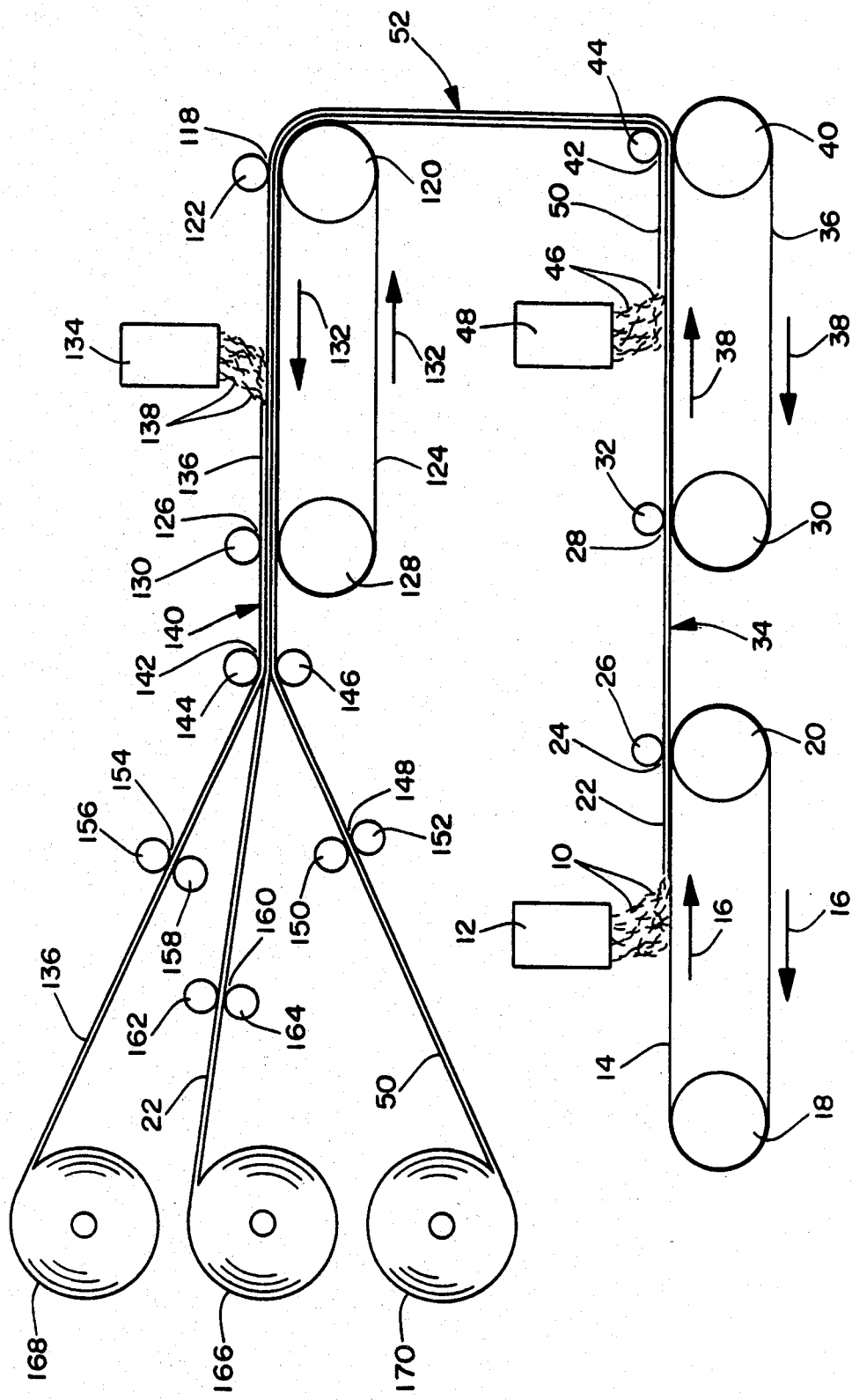
FIG. 5 is a schematic view of yet another mode for carrying out the present invention.

The three web intermediate material could be formed by the process which is illustrated schematically in FIG. 5. This process is identical to the process schematically illustrated in FIG. 1 until the two layered composite nonwoven elastic web 52 exits rollers 40 and 44. Thereafter, instead of proceeding to the nip or gap 54 between the rollers 56 and 58, the composite web 52 passes through the nip or gap 118 between a rotating roller 120 and a rotating nip roller 122. The composite web 52 is then carried by a third porous collecting screen 124 to the nip or gap 126 between a rotating nip roller 128 and a rotating roller 130. The porous collecting screen 124 moves about and is driven by the rollers 120 and 128 in the direction indicated by the arrows 132 in FIG. 5. Rotation of the rollers 118, 120, 126 and 128 is adjusted so that the peripheral surface speed of the rollers 118, 120, 126 and 128 is the same as the peripheral surface speed of the rollers 40 and 44. Accordingly, the fibrous nonwoven elastic web 22 is maintained at its stretched, biased and extended length as it is carried by the porous collecting screen 124.

While the composite nonwoven elastic web 52 is being carried by the porous collecting screen 124, a conventional meltblowing die 134 (if desired a conventional spunbonding die or carding apparatus can be utilized) forms a second nonwoven gatherable web 136 on the other surface of the stretched, extended fibrous, nonwoven, elastic web 22 by meltblowing microfibers 138 directly onto the stretched upper surface of the nonwoven elastic web 22. The materials which may be utilized to form the second gatherable web 136 may include any of the materials which were stated above as being utilizable to form the first fibrous nonwoven gatherable web 50. The second fibrous nonwoven gatherable web 136 is accordingly also separably joined to the surface of the fibrous nonwoven elastic web 22 by entanglement of the individual fibers of the web with the individual fibers of the web 22 during formation of the web 136 on the surface of the web 22.

After the separable joining of the gatherable web 136 to the elastic web 22 has been achieved, the biasing force on the web 22 is relaxed by passing the three webbed composite 140 through the nip or gap 142 between two rotating nip rollers 144 and 146. Rotation of the rollers 144 and 146 is adjusted so that the peripheral surface speed of the rollers 144 and 146 allows the composite web 140 to relax and, as a result of its elastic properties, to contract to its relaxed, unbiased length. The relaxing and contracting of the web 140 to its relaxed, unbiased length results in both of the fibrous nonwoven gatherable webs 50 and 136 being gathered by the relaxing and contracting of the fibrous nonwoven elastic web 22. Thereafter, the fibrous nonwoven gathered webs 50 and 136 are separated from the fibrous nonwoven elastic web 22 by passing the web 50 through the nip 148 between two rotating nip rollers 150 and 152 and passing the web 136 through the nip 154 between two rotating nip rollers 156 and 158. The webs 50 and 136 are then wound-up for storage and later used on their respective storage rolls 168 and 170. For the reasons stated earlier, care should be exercised in winding-up the gathered nonwoven webs 50 and 136 to assure that the webs 50 and 136 are stored in an untensioned or substantially untensioned fashion of the rolls 168 and 170. This can be effected by rotating the rolls 168 and 170 so that the peripheral surface speed of the roll 168 is equal to or just slightly greater than the peripheral surface speed of the rolls 156 and 158 and that the peripheral surface speed of the roll 170 is equal to or just slightly greater than the peripheral surface speed of the rollers 150 and 152. The fibrous nonwoven elastic web 22 passes through the nip 160 between the two rotating nip rollers 162 and 164 and is wound up on a storage roller 166.

While the specific examples discussed herein have usually stated that the fibrous nonwoven gatherable webs 50 and 136 were formed by utilization of a conventional meltblowing die and meltblowing processes, conventional spunbonding dies and spunbonding processes may be substituted for the meltblowing dies and processes and the scope of the present invention is intended to include materials formed by the substitution of spunbonding dies and processes or any other apparatus and process for forming a nonwoven gatherable web for the meltblowing dies and processes 48 and 134. In the event that spunbonding dies and processes were substituted for either or both of the meltblowing dies or processes 48 and 134 the separable joining of the gatherable web(s) 50 and, if applicable 136, to the fibrous nonwoven elastic web 22 could be effected by inter-web adhesion by (a) utilizing a tacky elastomeric material to form the web 22, (b) very slightly heat-bonding the webs 50 and 136 to the web 22, (c) slightly sonic bonding the web(s) 50 and 136 to the web 22 in a conventional manner and/or (d) a very light application of an adhesive to the surface(s) of the web 22 prior to formation of the web(s) 50 and 136 thereon. These methods of separably joining the web(s) 50 and 136 to the web 22 should be utilized with spunbonded gatherable webs since the fibers of spunbonded gatherable webs do not readily entangle and therefore do not readily separably join to the fibers of the web 22. However, at all times, care should be taken to assure that the joining of the web(s) 50 and 136 to the elastic web 22 is, in fact, a separable joining. Accordingly, the degree of separable joining effected by heat-bonding, sonic bonding or adhesive application should be maintained at the minimum necessary to assure that the gatherable web(s) will be gathered and that the joining of the webs to each other will be separable. If the separable joining of the webs 50 or 136 or 50 and 136, as applicable, to the web 22 is to be effected by heat-bonding care should be taken to allow the web 22 to relax and contract to substantially an untensioned, unbiased, condition or configuration as soon as is practical after the heat-bonding step has occurred because it is believed that the nonwoven elastic web 22 will lose its elasticity if it is maintained above its softening temperature for any significant period of time. This loss of elasticity may result from the cooling elastic web 22 "setting" while in the stretched configuration if it is maintained in the stretched configuration for a significant period of time after heat-bonding.

Exemplary tacky elastomeric material which may be utilized to form the nonwoven elastic web 22 to effect a separable joining with a spunbonded gatherable web are the S-I-S block copolymers mentioned above where S represents polystyrene endblocks and I is a polyisoprene midblock. These materials are available from the Shell Chemical Company under the trade designation KRATON D as stated above. Alternatively, blends of the aforementioned S-I-S KRATON D block copolymers with poly (alpha-methylstyrene) may be utilized.

The light heat-bonding of the webs to each other can be effected by maintaining the rollers 40 and 42 and, if applicable, the rollers 128 and 130 at an appropriate elevated temperature which usually ranges upward from about 50 degrees centigrade below the melting point of at least one of the materials used to form at least one of the webs to about the melting point of at least one of the materials used to form at least one of the webs.

This case is one of a group of cases which are being filed on the same date. The group includes application Ser. No. 760,449 in the name of M. T. Morman and entitled "Composite Nonwoven Elastic Web"; application Ser. No. 760,445 in the name of M. T. Morman entitled "Gathered Fibrous Nonwoven Web"; application Ser. No. 760,698 in the name of M. T. Morman and T. J. Wisneski entitled "Polyolefin-Containing Extrudable Compositions and Methods for Their Formation Into Elastomeric Products"; application Ser. No. 760,438 in the name of M. T. Morman and T. J. Wisneski entitled "Elasticized Garment and Method of Making the Same"; application Ser. No. 760,366 in the name of M. T. Morman and T. J. Wisneski entitled "High Temperature Method of Making Elastomeric Materials and Materials Obtained Thereby", and application Ser. No. 760,437 in the name of M. J. Vander Wielen and J. D. Taylor entitled "Composite Elastomeric Material and Process for Making the Same" and application Ser. No. 760,691 in the name of W. B. Haffner, M. T. Morman and T. J. Wisneski entitled "Block Copolymer-Polyolefin Elastomeric Films". The subject matter of all of these applications is hereby incorporated by reference.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. A process for producing a gathered nonwoven web having elastic characteristics, said process comprising the steps of:
   providing an extendable and contractable forming surface;
   extending the forming surface;
   forming a fibrous nonwoven gatherable web directly upon the extended forming surface to separably join the fibrous nonwoven gatherable web to the extended forming surface;
   contracting the forming surface to gather the fibrous nonwoven gatherable web; and
   separating the gathered fibrous nonwoven gatherable web from the contracted forming surface.

2. The process according to claim 1, wherein the step of providing said extendable and contractable forming surface comprises providing an apertured elastic film.

3. The process according to claim 1, wherein the step of providing said extendable and contractable forming surface comprises providing a wire mesh screen including substantially parallel extending coiled springs transversely connected by substantially parallel wires.

4. The process according to claim 1, wherein the step of providing said extendable and contractable forming surface comprises providing a fibrous nonwoven elastic web of meltblown microfibers.

5. The process according to claim 4, wherein the fibrous nonwoven elastic web is extended at least about 125 percent.

6. The process according to claim 5, wherein the fibrous nonwoven elastic web is extended from at least about 125 percent to about 700 percent.

7. The process according to claim 1, wherein the step of forming said fibrous nonwoven gatherable web comprises forming a fibrous nonwoven gatherable web of meltblown microfibers.

8. The process according to claim 1, wherein the step of forming said fibrous nonwoven gatherable web comprises forming a fibrous nonwoven gatherable web of spunbonded microfibers.

9. The process according to claim 1, wherein the step of separably joining the fibrous nonwoven gatherable web to the extendable and contractable forming surface is achieved by heat-bonding.

10. A gathered fibrous nonwoven web formed by the process according to claim 1, having elastic properties.

11. The gathered fibrous nonwoven web according to claim 10, said gathered web comprising nonelastic microfibers.

12. The gathered fibrous nonwoven elastic web according to claim 11, comprising nonelastic meltblown microfibers.

13. The gathered nonwoven elastic web according to claim 12, comprising nonelastic meltblown microfibers selected from the group consisting of nonelastic polyester microfibers, nonelastic polyolefin microfibers or blends of one or more nonelastic polyester microfibers with one or more nonelastic polyolefin microfibers.

14. The gathered nonwoven elastic web according to claim 13, wherein the nonelastic polyester microfibers comprise nonelastic polyethylene terephthalate microfibers.

15. The gathered nonwoven elastic web according to claim 13, wherein the nonelastic polyolefin microfibers comprise nonelastic polypropylene microfibers.

16. The gathered nonwoven elastic web according to claim 10, said gathered web consisting essentially of nonelastic meltblown microfibers.

17. The gathered nonwoven elastic web according to claim 11, comprising nonelastic spunbonded microfibers.

18. The gathered nonwoven elastic web according to claim 17, comprising nonelastic spunbonded microfibers selected from the group consisting of nonelastic polyester microfibers, nonelastic polyolefin microfibers or blends of one or more nonelastic polyester microfibers with one or more nonelastic polyolefin microfibers.

19. The gathered nonwoven elastic web according to claim 18, wherein the nonelastic polyester microfibers comprise nonelastic polyethylene terephthalate microfibers.

20. The gathered nonwoven elastic web according to claim 18, wherein the nonelastic polyolefin microfibers comprise nonelastic polypropylene microfibers.

21. The gathered nonwoven elastic web according to claim 17, consisting essentially of nonelastic spunbonded microfibers.

22. A process for producing a gathered nonwoven web having elastic characteristics, said process comprising the steps of:
   providing a nonwoven elastic web forming surface having a relaxed, unbiased and contracted length and a stretched, biased and extended length;
   stretching said nonwoven elastic web forming surface to said extended length;
   forming a fibrous nonwoven gatherable web directly upon a surface of said nonwoven elastic web forming surface to separably join said fibrous nonwoven gatherable web to said surface to said nonwoven elastic web forming surface while maintaining said nonwoven elastic web forming surface at said stretched length wherein the separable joining of the fibrous nonwoven gatherable web to the nonwoven elastic web forming surface is achieved by entanglement of the individual fibers of the nonwoven gatherable web with the individual fibers of the fibrous nonwoven elastic web forming surface during formation of the fibrous nonwoven gatherable web on the surface of the nonwoven elastic web forming surface;
   contracting the nonwoven elastic web forming surface to gather the fibrous nonwoven gatherable web; and
   separating the gathered fibrous nonwoven gatherable web from the nonwoven elastic web forming surface.

23. The process according to claim 22, wherein the step of providing said nonwoven elastic web forming surface comprises forming a nonwoven elastic web of meltblown microfibers.

* * * * *

UNITED STATES PATENT AND TRADEMARK OFFICE
CERTIFICATE OF CORRECTION

PATENT NO. : 4,652,487
DATED : March 24, 1987
INVENTOR(S) : Michael T. Morman

It is certified that error appears in the above—identified patent and that said Letters Patent is hereby corrected as shown below:

Column 4, line 24 "monaxially" should read -- monoaxially --
Column 11, line 54 "firbrous" should read -- fibrous --
Column 12, line 10 "contacting" should read -- contracting --
Column 14, line 47 "Yet another" should read -- Yet other --
Column 16, line 33 "ASTM D 1050" should read -- ASTM D 1505 --
Column 17, line 46 "Examplary" should read -- Exemplary --
Column 26, line 47 "to said nonwoven" should read -- of said nonwoven --

Signed and Sealed this

Twenty-seventh Day of October, 1987

Attest:

DONALD J. QUIGG

Attesting Officer

Commissioner of Patents and Trademarks